United States Patent [19]
Isogai et al.

[11] Patent Number: 5,347,331
[45] Date of Patent: Sep. 13, 1994

[54] OPHTHALMIC APPARATUS FOR PHOTOGRAPHING THE ANTERIOR PART OF THE EYE WITH A REPRODUCIBLE PHOTOGRAPHING POSITION

[75] Inventors: Naoki Isogai, Nishio; Hirohiko Hanaki, Gamagori, both of Japan

[73] Assignee: Nidek Co., Ltd., Aichi, Japan

[21] Appl. No.: 74,494

[22] Filed: Jun. 11, 1993

[30] Foreign Application Priority Data

Jun. 30, 1992 [JP] Japan .................. 4-197520

[51] Int. Cl.[5] .................. A61B 3/14; G03B 29/00
[52] U.S. Cl. .................. 354/62; 351/208; 351/211; 351/214; 351/221
[58] Field of Search .................. 354/62; 351/206, 208, 351/211, 212, 214, 221

[56] References Cited

U.S. PATENT DOCUMENTS 5,159,361 10/1992 Cambier et al. .................. 351/212
5,202,708 4/1993 Sasaki et al. .................. 354/62 X

OTHER PUBLICATIONS

U.S. patent application Ser. No. 07/901,984, Isogai et al, filed on Jun. 22, 1992.

Primary Examiner—Michael L. Gellner
Assistant Examiner—J. K. Han
Attorney, Agent, or Firm—Finnegan, Henderson, Farabow, Garrett & Dunner

[57] ABSTRACT

Ophthalmic photographing apparatus for photographing an anterior part of examinee's eye provides an alignment optical system including a reflection image forming device for forming an image reflected on the cornea of the examinee's eye, an observation optical system for observing image of the anterior part of the examinee's eye, comprising an alignment reticle, and a photographing optical system for photographing the anterior part of the examinee's eye. The picture image data of the anterior part of the eye photographed with the photographing optical system is memorized by a picture image data memory, and an alignment deviation is detected by operating the memorized picture image signal to detect a designated part and by finding a dislocation distance of the designated part from a reference position, and an analyzing position of the image is corrected on the basis of the alignment deviation and the picture image of the anterior eye is analyzed.

10 Claims, 6 Drawing Sheets

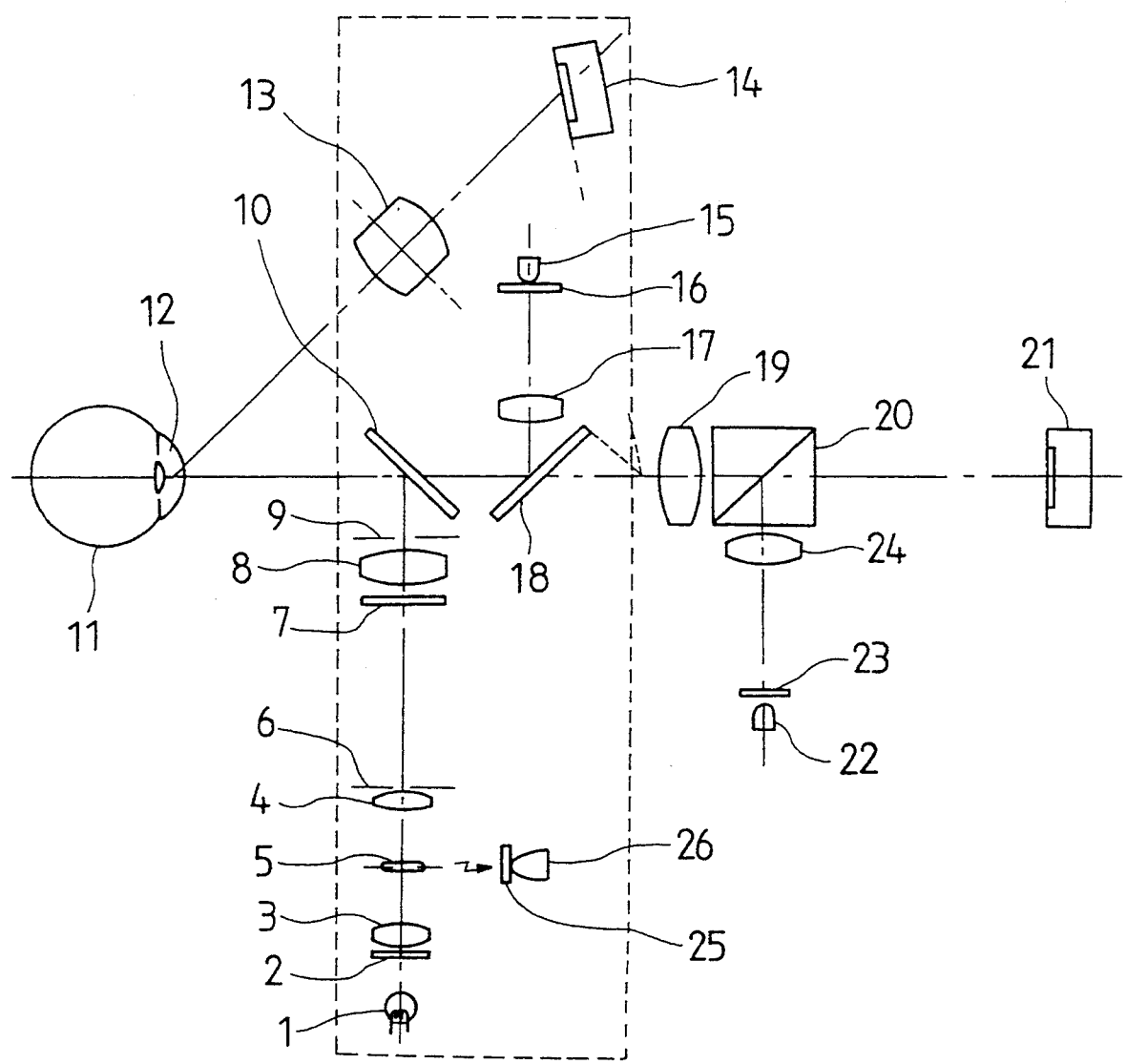
F I G. 1

OPHTHALMIC APPARATUS FOR PHOTOGRAPHING THE ANTERIOR PART OF THE EYE WITH A REPRODUCIBLE PHOTOGRAPHING POSITION

BACKGROUND OF THE INVENTION

1. Field of the Invention

The present invention relates to an ophthalmic apparatus for photographing the anterior part of an examinee's eye, particularly to an ophthalmic photographing apparatus comprising a device capable of photographing sectional images of the anterior part of the eye with a reproducible photographing position.

2. Description of Related Art

Conventionally, there are some kinds of ophthalmic photographing apparatuses which project a slit light to the examinee's eye, and photograph a sectional image of the anterior part of the eye on the basis of Scheimpflug's principle. Picture images of the eye obtained through the conventional apparatuses are analyzed to provide useful data including inclination and decentration of the IOL (Intra Ocular Lens). For analysis to find the inclination and decentration of the IOL and for another analysis, for instance Densitometry and Biometry, it is useful to reproduce the photographing position in order to detect the progressing variation in the data.

To align a conventional photographing optical system to an examinee's eye, a reticle of the photographing optical system is adjusted to Purkinje images focused on the cornea of the examinee's eye, particularly the first Purkinje image on the anterior surface of the cornea, by the hand of an operator with experience.

However, in the above conventional alignment operation, depending on the experience of the operator, the quality of photographed picture images will differ from operator to operator. Even same operator can not execute closely the alignment between the photographing optical system and the examinee's eye every time. Thus, photographed picture images would be in disagreement. And even if a photographing apparatus of a same type is used, photographed picture images would be in disagreement according to the respective adjustment condition of the apparatus.

In order to solve the above disagreement between picture images, the adjustment of the photographing apparatus and the alignment operation would take a long time and, if a special alignment device is added to the conventional photographing apparatus, the price will increase greatly. In film photography, in particular, disagreement of picture image could be found out only after development of the photographed film. Thereby it is necessary to photograph the examinee's eye again for the analysis of image of the eye.

SUMMARY OF THE INVENTION

The present invention has been made in view of the above circumstances and has an object to overcome the above problems and to provide an ophthalmic photographing apparatus capable of reproducing picture images with a consistent photographing position.

To achieve the objects and in accordance with the purpose of the invention, as embodied and broadly described herein, the ophthalmic photographing apparatus of this invention comprises an alignment optical system including a reflection image forming means for forming an image reflected on the cornea of the examinee's eye and an observation optical system for observing image of the anterior part of the examinee's eye, comprising an alignment reticle; a photographing optical system for photographing the anterior part of the examinee's eye; a picture image memory means for memorizing the picture image of the anterior part of the eye photographed with the photographing optical system; an alignment deviation detecting means for detecting alignment deviation by processing the memorized picture image signal to detect a designated part and by finding a dislocation distance of the designated part from a reference position; a correction means for correcting an analyzing position, at which the memorized picture image of the anterior eye is analyzed, on the basis of the alignment deviation detected through the detecting means; and an analysis means for analyzing the picture image of the anterior eye.

According to the ophthalmic photographing apparatus of this invention, it is possible to obtain easily picture images of the anterior eye with high reproductivity of the photographing position.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 1 is a schematic view of the ophthalmic photographing apparatus of the present embodiment.

DETAILED DESCRIPTION OF THE PREFERRED EMBODIMENTS

Figure 2:
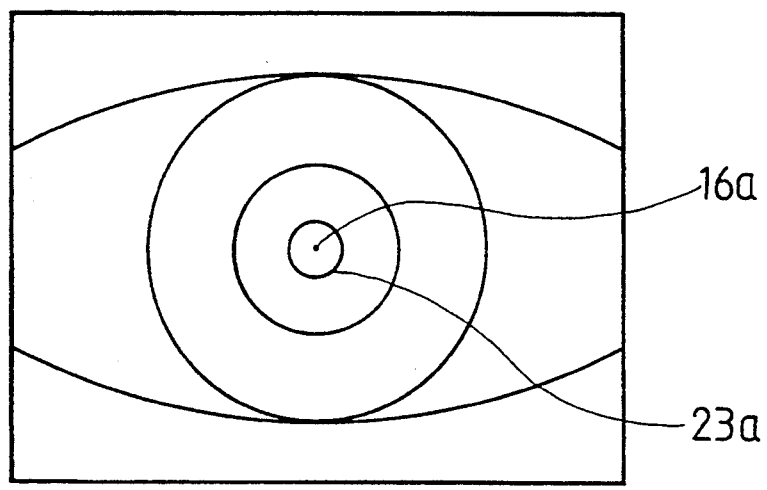
FIG. 2 is a schematic view of showing an monitor image photographed through CCD camera 21.

A detailed description of one preferred embodiment of an ophthalmic photographing apparatus embodying the present invention will now be given referring to the accompanying drawings.

FIG. 1 shows schematically an optical system of a photographing apparatus for photographing sectionally the anterior eye on the basis of the Scheimpflug's principle.

The optical system comprises a slit projection optical system, a photographing optical system, an alignment/fixation index projection system, the alignment observing system, and alignment reticle projection system.

First, the slit projection optical system comprises an illumination light source 1 for projecting a slit image onto an anterior eye 12 of the examinee's eye 11, an infrared irradiation transmitting filter 2, condenser lenses 3 and 4, a photographing flash light source 5, a slit 6 of which a slit width is variable as well as a conventional slit lamp, a polarizing filter 7 for preventing the slit light from being incident into an alignment CCD camera 21 mentioned later, a slit projection lens 8, a rectangular aperture diaphragm 9 for deepening the depth of focus of the slit projected image, and a polarized beam splitter 10.

The light emitted from the flash light source 5 in the slit projection optical system is introduced into a brightness level detector 26 through a filter 25 for reducing quantity of light. On receiving the reduced light, the brightness level detector 26 monitors the quantity of light. A signal of quantity of light from the detector 26 is calculated in comparison with reference data of light quantity stored in advance, and corrected picture element (pixel) data is found out.

In the photographing optical system, a focusing lens 13 and a CCD camera 14 are arranged so that an optical sectional plane of the projection image of the slit 6, each extended plane of a principal plane of the focusing lens 13 and a focused plane of the CCD camera 14 intersect each other by one intersection line. In this embodiment, the photographing optical axis is arranged at an angle of 45° to the slit projection optical axis.

The alignment and fixation index projection optical system includes an alignment light source 15 consisted of a visible ray source such as an LED, a fixation and alignment index 16 of a pin hole form, an index projection lens 17, and a half mirror 18.

The alignment observing optical system comprises a focusing lens 19, a half mirror 20 and an alignment CCD camera 21.

The alignment reticle projection optical system consists of a light source for reticle projection 22 using an infrared light, an alignment reticle 23 of a ring form, and a reticle projection lens 24.

In the above mentioned apparatus, the slit projection optical system of numerals 1-10, the photographing optical system of 13 and 14 and the alignment/fixation index projection system of 15-18 are able to revolve around a visual axis of the examinee's eye 11. Therefore the anterior eye can be sectionally photographed at two or more positions.

In FIG. 2, a monitor image photographed by the CCD camera 21 is shown, wherein numeral 16a is a reflected image of the fixation/alignment index on the front surface of cornea, and numeral 23a is the alignment reticle image.

Figure 3:
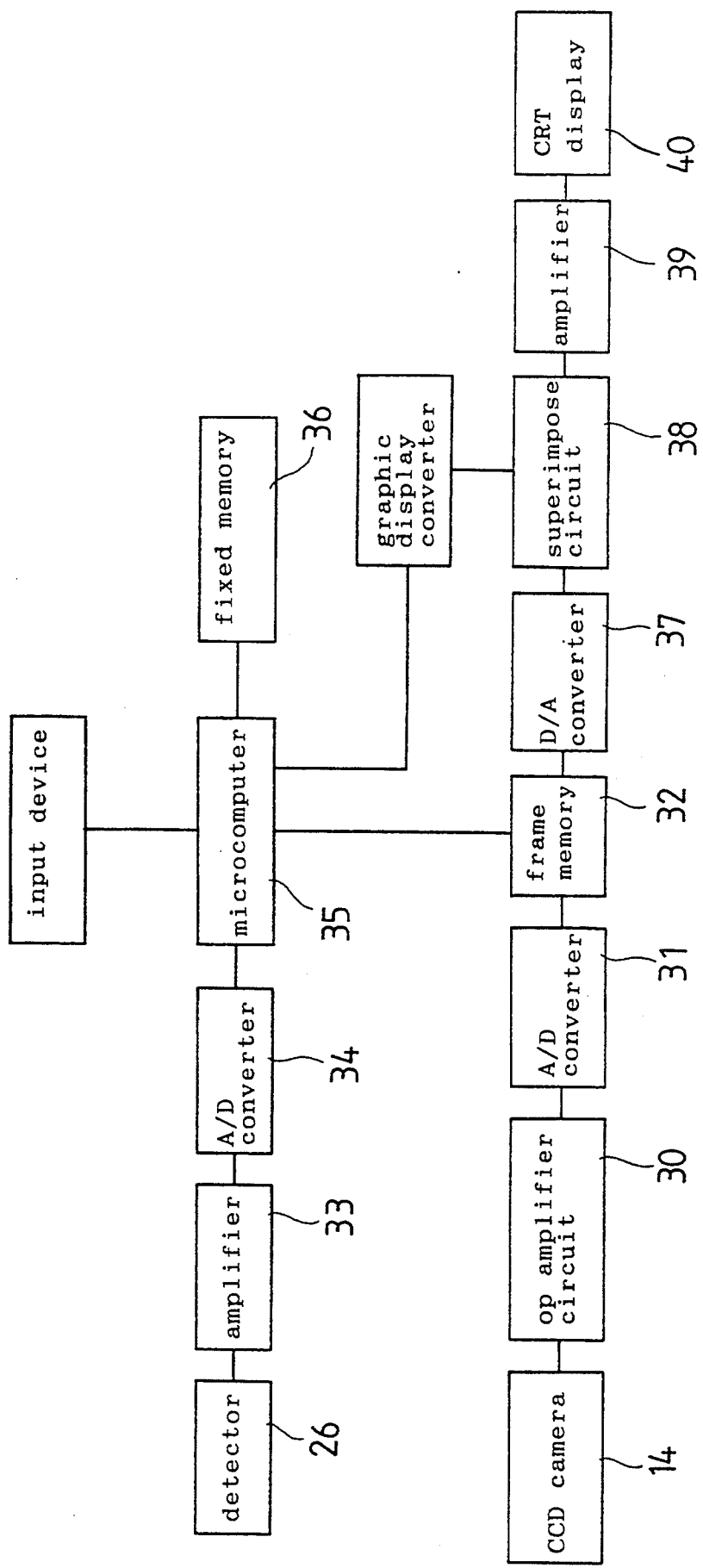
FIG. 3 is a block diagram of the image signal level control system.

FIG. 3 shows a block diagram of an image signal level control system for correcting changes of the quantity of light emitted from the photographing light source.

Synchronizing with an emission of the flashing light source 5, an image signal of the anterior eye is detected by the CCD camera 14 through the photographing lens 13. And then, the image signal is converted into digital signal through an operational amplifier circuit 30 and an analog/digital(A/D) converter circuit 31, and is given to an frame memory 32. At the same time, the light monitor signal of the brightness level detector 26 is fetched out, and then is amplified at an amplifier 33, converted into digital signal through A/D converter circuit 34, and input into a microcomputer 35.

The microcomputer 35 reads out the digital signal of the image signal from the frame memory 32, corrects and calculates it on the basis of reference data of the quantity of light memorized in a fixed memory 36 and a digital signal of the light monitor signal of the detector 26.

The microcomputer 35 calculates also dislocation distance of the picture image signal in X-Y direction as described below.

After the luminance and the dislocation distance of the image signal are corrected as mentioned above, the signal is converted into analog signal at a D/A converter 37 through the frame memory 32. And the analog signal is superposed with a graphic index showing letter or axis at a superimpose circuit 38, displayed on a CRT display 40 through the operational amplifier circuit 39.

According to the above apparatus, the operation is explained as follows.

Since an image of the fixation/alignment index 16 is first projected onto the examinee's eye 11, the examinee should fixedly stare at the image. The image of the index 16 reflected on the front surface of cornea of the eye 11 is monitored in the alignment CCD camera 21 through an focusing lens 19. To align the apparatus with the examinee's eye, the apparatus is moved in a horizontal or vertical direction so as to put the point image 16a of the index 16 into a small circle of an alignment reticule image 23a on the monitored image in the CCD camera 21. And to set the alignment in the optical axis direction, the apparatus is moved forward or backward along the optical axis until the point image 16a comes into focus.

To bring the photographing system in focus, based on the CRT display 40 of photographing CCD camera 14, the focusing lens 13 is moved in the extending direction of its principal plane, or the CCD camera 14 is moved in the extending direction of the focus point. Usually, the depth of focus is deep because the F-number of the focusing lens 13 is large, so that the focusing operation is almost unnecessary if the alignment is finally fixed.

Synchronizing with the emission of the flash light source 5, the image signal detected through the CCD camera 14 is input to the frame memory 32 through the operational amplifier 30 and the A/D converter circuit 31.

The image signal read out from the frame memory 32 is corrected and calculated in the image signal level control system (microcomputer 35), based on the light monitor signal fetched out the detector 26, and then the corrected and calculated signal is displayed on the CRT display 40 through the frame memory 32.

Figure 4:
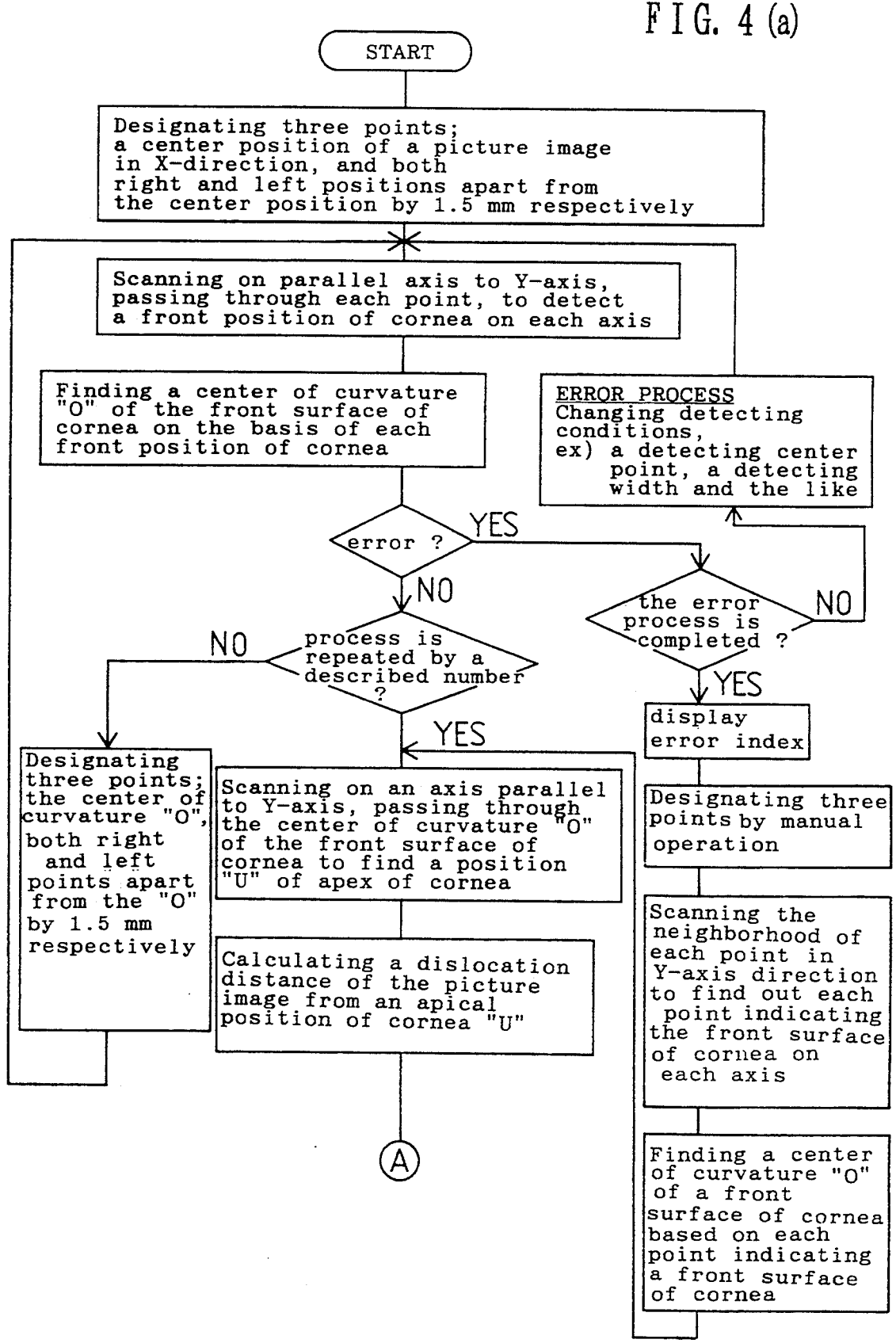
FIG. 4(a) and FIG. 4(b) are flow charts for calculating dislocation distance in X-Y direction.
Figure 4B:
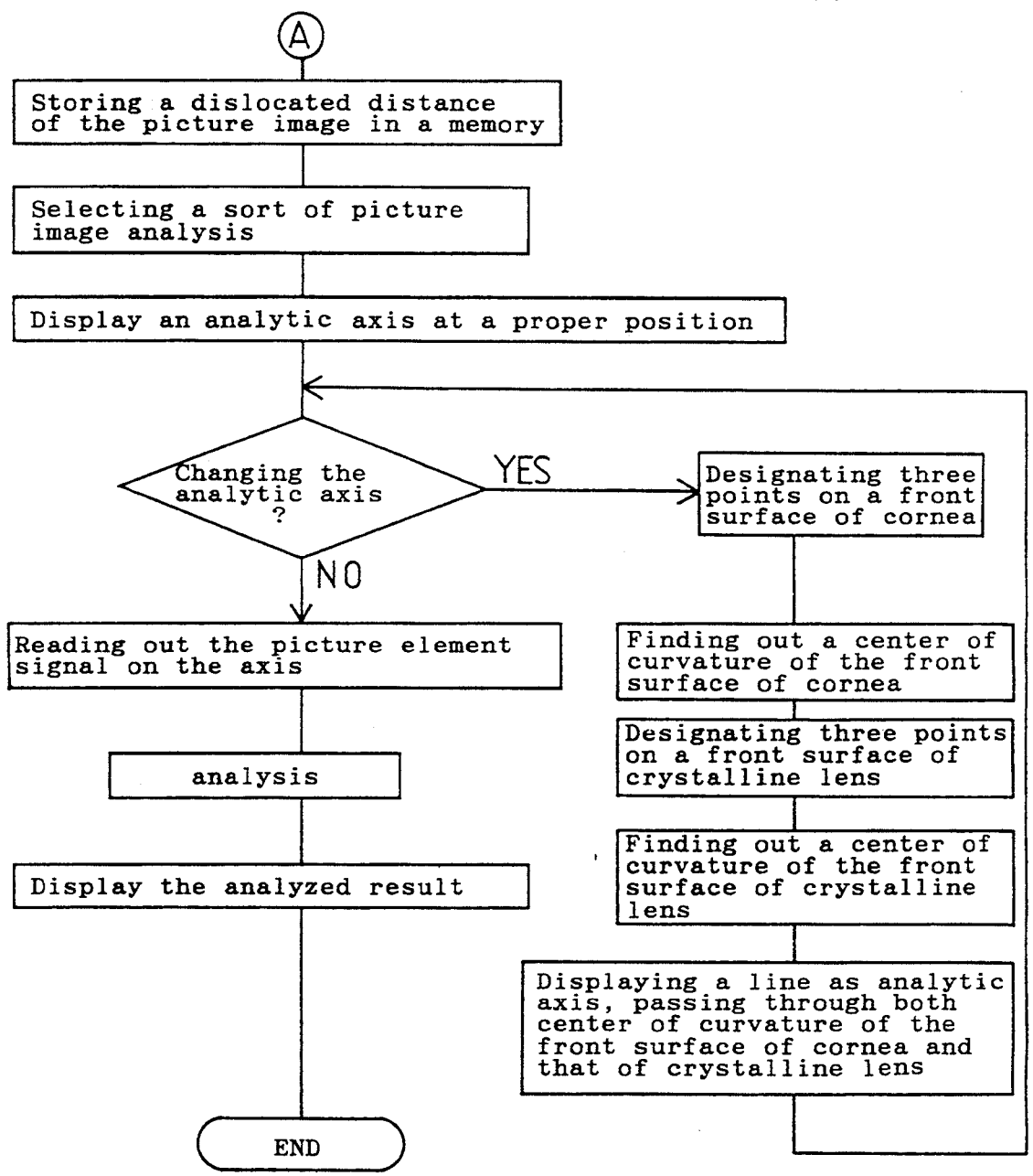

The microcomputer 35 calculates the dislocation distance of the picture image signal in X-Y direction in accordance with the following operation, referring to FIGS. 4(a) and 4(b). Each picture element signal of the picture image includes a position information in X-Y direction and density of 256 grades (0–255). In a slit sectional image, a high light scattering part, for example a cornea or a crystalline lens, is whitish (=high density), and a scarcely light scattering part, for example a front part to the cornea or an anterior chamber, is blackish (=low density).

At first, an apex of cornea is detected on the basis of a center of picture image in X direction and each picture element signal at positions apart right and left from the center by a predetermined distance (called a detecting width, predetermined within ±1.5 mm in the present embodiment). A surface part within 3 mm in area where the apex of cornea centers is nearly homogeneous toric face, and the surface part can be regarded as a spherical surface. Thereby it is preferable that a detected point is in the area.

Figure 5:
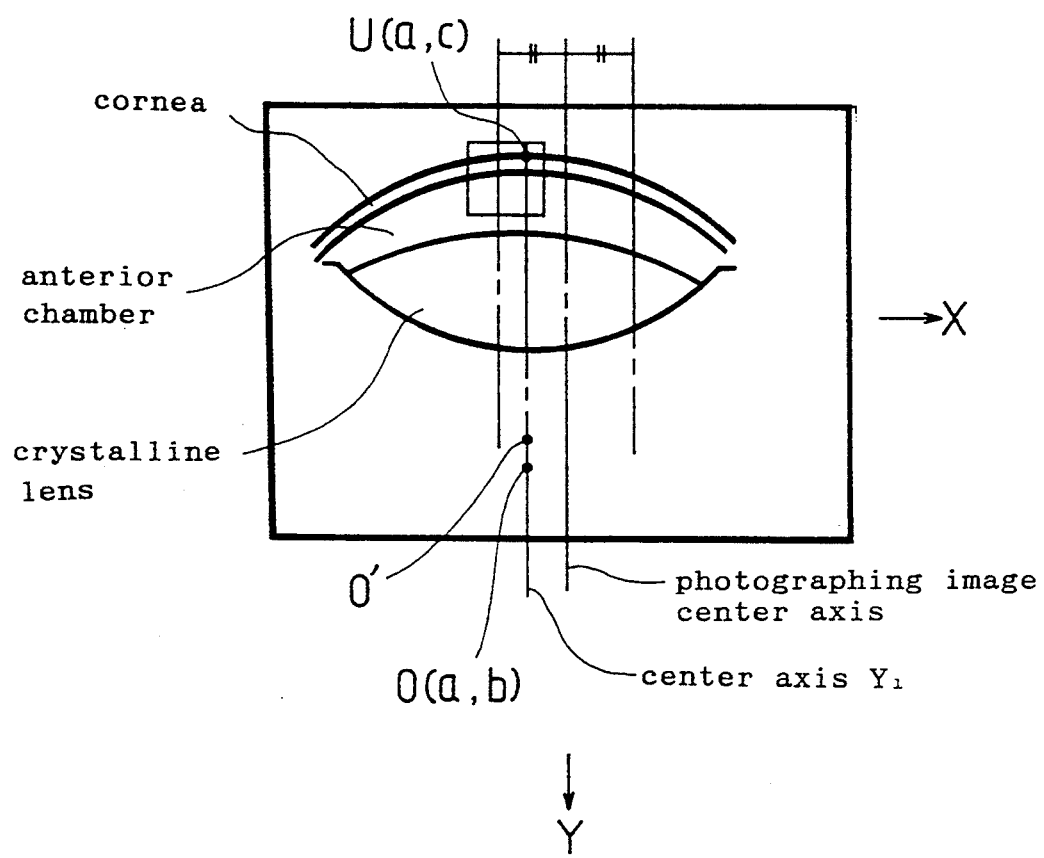
FIG. 5 is a schematic view of explaining the calculation for dislocation distance in X-Y direction.

The microcomputer 35 reads out each picture element signal on a parallel axis to the Y-axis, passing through each point from the frame memory 32, and investigates successively the picture element from a light source side to a fundus of eye side by utilizing a common picture image analytical technique (for instance, binary method, smoozing method or the like) and finds a pulse rising point at which a density is higher than a predetermined reference value respectively. When each picture element signal is successively investigated along the Y-axis direction from the light source side to the fundus side of the eye, as shown in FIG. 5, a first part showing a high density indicates the cornea. The pulse rising point in density variation means a front position of the cornea.

After extraordinary data caused by noise and the like is cancelled, respective coordinates at three points on a front surface of cornea at three points are substituted into an equation of a circle to find a center of curvature "O" (a, b) of the front surface of cornea. In the present embodiment, the data at only three points are utilized as mentioned above, but if a plurality of data are calculated through the minimum multiplication method, a more precise value may be obtained.

It is possible to assume the cornea is an approximation of a spherical surface in the neighborhood of the apex of cornea. Thereby, the sectional plane can be considered as circle and each coordinate at three points is substituted into an usual formula, $(x-a)^2+(y-b)^2=c^2$, to find a center of curvature "O" (a, b).

If the found center of curvature "O" is positioned at an abnormal position to the cornea or the crystalline lens, and a radius of curvature is not found within a reference value, the found value is judged to be error. If the found value is error, the center of curvature is detected again at different detecting conditions including a detecting center point and a detecting width. If a proper position of the apex of cornea can not be detected in a memorized condition in advance, an error index is displayed, and then a manual operation follows. In the manual operation, the operator (photographer) moves a cursor through an operation panel (not shown) to designate three points on a front surface of cornea. Scanning the neighborhood of each designated point to Y-axis direction, the front surface position of cornea is detected on the basis of signals obtained through the scanning, following which the center of curvature "O" is found.

On the basis of the x coordinate of the center of curvature found at the first operation, a similar detecting operation is repeated to find a center of curvature "O'", putting a center of curvature "O" of the front surface of cornea as a center axis. It is possible to improve the precision of detecting the center of curvature "O'" accordingly.

The microcomputer 35 taking a parallel line to Y-axis through passing the center of curvature "O'" for a center axis $Y^1$ of the sectional image of the anterior eye, reads out a picture element signal on the center axis $Y^1$ and calculates it to find a coordinate (a, c) of the apex of cornea "U" at which the center axis $Y^1$ intersects with the front surface of cornea, referring to FIG. 5. An operation between the coordinate of "U" and a coordinate of a predetermined position is carried out to find a dislocation distance in X-Y direction. In the present embodiment, the predetermined position means an apical position of cornea in the ideal alignment condition in which the apex of cornea is on an optical axis of a slit image projecting system and in focus.

The dislocation distance of the picture image found as mentioned above is stored in a memory. When the operator selects a sort of picture image analysis, an analysis axis is displayed on the monitor. In the ideal alignment condition, the analytic axis is displayed at a position correspondent to position with a center axis of photographing image, but in a condition out in alignment, the analytic axis is shifted to and displayed at a position passing through the apex of cornea on the basis of the dislocation distance.

When the sectional image of the anterior eye is off to the round direction, the detecting operation as expected can not be executed. Then, three points on a front face of cornea and three points on a front face of a crystalline lens are designated respectively, thereby each center of curvature is found, following which a line passing through the both center of curvature is displayed as an analysis axis. In such operation, it is possible to substitute a center of the pupil for the center of curvature of the front surface of crystalline lens, the center of the pupil which is found on the basis of each position of both ends of the iris.

When the analysis axis is displayed at a proper position to the sectional image of the anterior eye, microcomputer 35 reads out the picture element signal on the analysis axis to analyze it, and then displays the analyzed result on the monitor.

Although the analysis axis is shifted in the present embodiment, it is possible to fix the analysis axis and shift the displayed image itself by the dislocated distance.

The corrected picture image signal can be stored by usual means, for instance in a disk, thereby a progressing change in the sectional image of the examinee's eye can be found out precisely by comparison with the stored former image.

The present invention may be embodied in other specific forms without departing from the spirit or essential characteristics thereof. For instance, in the above embodiment, the present invention is applied to the photographing apparatus for photographing sectional image of the anterior part of the examinee's eye, it may be of course applied to an ophthalmic photographing apparatus using ultrasound or laser-scanning.

The dislocation distance is detected by specifying a front surface form of cornea in the above embodiment, it may be detected also by detecting a position of reflection luminescent spot of cornea when photographed.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment has been chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. Ophthalmic photographing apparatus for photographing an anterior part of an examinee's eye, comprising:
   an alignment optical system including,
      a reflection image forming means for forming an image reflected on a cornea of the examinee's eye,
      an observation optical system for observing an image of the anterior part of the examinee's eye, comprising an alignment reticle;
   a photographing optical system for photographing the anterior part of the examinee's eye;

means for storing a memorized picture image of the anterior part of the examinee's eye photographed with said photographing optical system;

means for detecting alignment deviation by processing a signal of said memorized picture image to detect a designated part and by finding a dislocation distance of said designated part from a reference position;

means for analyzing said memorized picture image at an analyzing position; and means for correcting said analyzing position on the basis of said dislocation distance.

2. Ophthalmic photographing apparatus according to claim 1, further comprising means for displaying a photographed image of the anterior part of the examinee's eye.

3. Ophthalmic photographing apparatus according to claim 1, further comprising:
a photographing light flash source;
means for detecting a light quantity of said photographing flash light source;
a light quantity comparison processing means for comparing said light quantity of said photographing flash light source and a predetermined reference light quantity; and
means for correcting a luminance signal of said memorized picture image based on a result of said light quantity comparison processing means.

4. Ophthalmic photographing apparatus for photographing an anterior part of an examinee's eye, comprising:
an alignment optical system including,
a reflection image forming means for forming an image reflected on a cornea of the examinee's eye,
an observation optical system for observing an image of the anterior part of the examinee's eye, comprising an alignment reticle;
a slit image projection system for projecting a slit image onto the examinee's eye;
a photographing system for photographing a sectional image of the examinee's eye cross-sectioned with said slit image;
means for storing a memorized picture image of said sectional image photographed with said photographing system;
means for detecting alignment deviation by processing a signal of said memorized picture image to detect an apical position of said cornea and by finding a dislocation distance of said apical position from a reference position;
means for analyzing said memorized picture image at an analyzing position; and
means for correcting said analyzing position on the basis of said dislocation distance.

5. Ophthalmic photographing apparatus according to claim 4, wherein said alignment deviation detecting means comprises means for detecting at least three points on the front surface of said cornea and means for calculating a center of curvature of said cornea by specifying the form of said cornea based on said points.

6. Ophthalmic photographing apparatus according to claim 5, wherein said alignment deviation detecting means further comprises means for judging whether said specified form of said cornea is within a desired range.

7. Ophthalmic photographing apparatus according to claim 4, further comprising:

a photographing light flash source;
means for detecting a light quantity of said photographing flash light source;
a light quantity comparison processing means for comparing said detected light quantity of said photographing flash light source and a predetermined reference light quantity; and
means for correcting g luminance signal of said memorized picture image based on a result of said light quantity comparison processing means.

8. Ophthalmic photographing apparatus according to claim 4, further comprising means for displaying a sectional image of the examinee's eye.

9. Ophthalmic photographing apparatus for photographing an anterior part of an examinee's eye, comprising:
an alignment optical system including,
a reflection image forming means for forming an image reflected on a cornea of the examinee's eye,
a photographing optical system for photographing an image of the anterior part of the examinee's eye,
an alignment reticle;
means for displaying said image of the anterior part of the examinee's eye and an image of said alignment reticle;
a slit image projection system for projecting a slit image onto the examinee's eye;
a photographing system for photographing a sectional image of the examinee's eye through a CCD camera based on Sheimpflug's principle, said sectional image being obtained through said slit image projected by said slit image projection system;
means for storing a memorized picture image of the sectional image photographed with said CCD camera;
means for detecting alignment deviation by processing a signal of said memorized picture image to detect at least three points near the apex of said cornea and by finding a dislocation distance of an apical position of said cornea from a reference position;
means for displaying the photographed sectional picture image of the examinee's eye;
a display circuit for displaying a graphic pattern on the display means; and
means for correcting the graphic pattern displayed on the display means on the basis of said dislocation distance.

10. Ophthalmic photographing apparatus for photographing an anterior part of an examinee's eye, comprising:
an alignment optical system including,
a reflection image forming means for forming an image reflected on a cornea of the examinee's eye,
an observation optical system for observing an image of the anterior part of the examinee's eye, comprising an alignment reticle and a CCD camera;
a photographing optical system for photographing the anterior part of the examinee's eye;
means for storing a memorized picture image of the anterior part of the examinee's eye photographed with said photographing optical system;
means for detecting alignment deviation by processing a signal of said memorized picture image to detect a designated part and by finding a dislocation distance of said designated part from a reference position;

means for analyzing said memorized picture image at an analyzing position; and means for correcting said analyzing position on the basis of said dislocation distance.

* * * * *